US006759561B2

(12) United States Patent
Funke et al.

(10) Patent No.: US 6,759,561 B2
(45) Date of Patent: Jul. 6, 2004

(54) PREPARATION OF TETRAHYDROGERANIOL

(75) Inventors: Frank Funke, Mannheim (DE); Till Gerlach, Ludwigshafen (DE); Klaus Ebel, Lampertheim (DE); Signe Unverricht, Mannheim (DE); Frank Haese, Lambsheim (DE); Kirsten Burkart, Ludwigshafen (DE); Hans-Georg Göbbel, Kallstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/309,261

(22) Filed: Dec. 4, 2002

(65) Prior Publication Data

US 2003/0158453 A1 Aug. 21, 2003

(30) Foreign Application Priority Data

Dec. 7, 2001 (DE) .......................... 101 60 142

(51) Int. Cl.[7] .................. C07C 27/04; C07C 35/00; C07C 27/00; C07C 27/02; C07C 27/18; C07C 29/14
(52) U.S. Cl. .................. 568/885; 568/875; 568/876; 568/878; 568/880; 568/884
(58) Field of Search ................. 568/875, 876, 568/878, 880, 881, 884, 885

(56) References Cited

U.S. PATENT DOCUMENTS 2,417,220 A * 3/1947 Smith et al. .............. 260/531

FOREIGN PATENT DOCUMENTS

| GB | 989262 | 2/1962 |
| JP | 52091811 | 8/1977 |
| JP | 57024320 | 2/1982 |
| JP | 60197634 | 10/1985 |
| SU | 729183 | 4/1980 |

OTHER PUBLICATIONS

Singh et al., *J. of Catalysis*, 191, 2000, p. 181–191.
Matteoli et al., *J. Mo. Catalysis A: Chemical*, 140, 1999, p. 131–137.
Ipatjew, Chem. Ber., 45, 1912, 322.
Savoia, Tagliavini, Trombini, Umani–Ronchi, J. Org. Chem., 1981, 46, 5344–5348.
J. Chem. Soc. Chem. Com. 1995 (Iyer, Varghese (4), 465–466.

* cited by examiner

*Primary Examiner*—Johann Richter
*Assistant Examiner*—Elvis O. Price
(74) *Attorney, Agent, or Firm*—Keil & Weinkauf

(57) ABSTRACT

The present invention relates to a process for the preparation of tetrahydrogeraniol, wherein the product mixtures and distillation residues from linalool, citronellal, citronellol or geraniol/nerol synthesis are fed directly to catalytic hydrogenation.

10 Claims, No Drawings

PREPARATION OF TETRAHYDROGERANIOL

The present invention relates to a process for the preparation of tetrahydrogeraniol, where the product mixtures and distillation residues from linalool, citronellal, citronellol or geraniol/nerol synthesis are fed directly to catalytic hydrogenation.

Tetrahydrogeraniol (3,7-dimethyloctanol) is an important intermediate in industrial organic synthesis and is used as a scent in its own right or as an additive in soaps and detergents.

The preparation of tetrahydrogeraniol by hydrogenation of unsaturated precursors such as citral, citronellol or citronellal, or nerol/geraniol has been known for a long time. As long ago as 1912, the hydrogenation of citral over palladium was described (Ipatjew, Chem. Ber., 45, 1912, 3222). The hydrogenation of citral over metals on potassium-graphite supports is described in Savoia, Tagliavini, Trombini, Umani-Ronchi J. Org.Chem., 1981, 46, 5344–5348. Tetrahydrogeraniol is obtained in a yield of 95% over Ni/graphite catalysts. In 1993, the hydrogenation of citronellol to give tetrahydrogeraniol over a Pd/C catalyst succeeded in yields of 93%. The hydrogenation of 3,7-dimethyloctanal over a homogeneous $(NiCl_2(PPh_3)_2)$ catalyst was documented in J. Chem. Soc. Chem. Com. 1995 (Iyer, Varghese (4), 465–466). It succeeds in a yield of 57%.

The hydrogenation of precursors that are already expensive to prepare and are present in pure form, such as citral, nerol or geraniol, does not make commercial sense. Total hydrogenation, eg. in the preparation of nerol/geraniol is inadvisable due to the poor separability of tetrahydrogeraniol from the unsaturated products.

It is an object of the present invention to provide an economical process for the preparation of tetrahydrogeraniol by the reaction or the use of residues that are obtained during the preparation of linalool, citronellal, citronellol or geraniol/nerol.

There is a need for a process whereby the hydrogenation of the residues from the abovementioned partial hydrogenations or rearrangements, particularly from linalool synthesis, can be conducted at high conversion and with good yields, selectivity and catalyst lifetime.

We have found that this object is achieved, surprisingly, by a process for the preparation of tetrahydrogeraniol, wherein the product mixtures and distillation residues resulting from linalool, citronellal, citronellol or geraniol/nerol synthesis are fed directly to catalytic hydrogenation.

Suitable starting materials include all product mixtures or distillation residues comprising more than one compound of the following basic structure of the general formula I

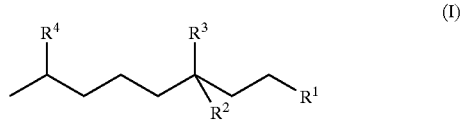

where
$R^1$ is OH, H, $CH_3$
$R^2$, $R^3$ are H, OH, $CH_3$
$R^4$ is H, $CH_3$,
and one to four double bonds can be present at any site in the molecule.

The product mixtures or distillation residues preferably comprise more than one compound selected from the group consisting of nerol, geraniol, isonerol 2, citral, citronellol, 3,7-dimethyloctanal, isonerol 1, citronellal, linalool (from top to bottom in the formula scheme, linalool is not shown).

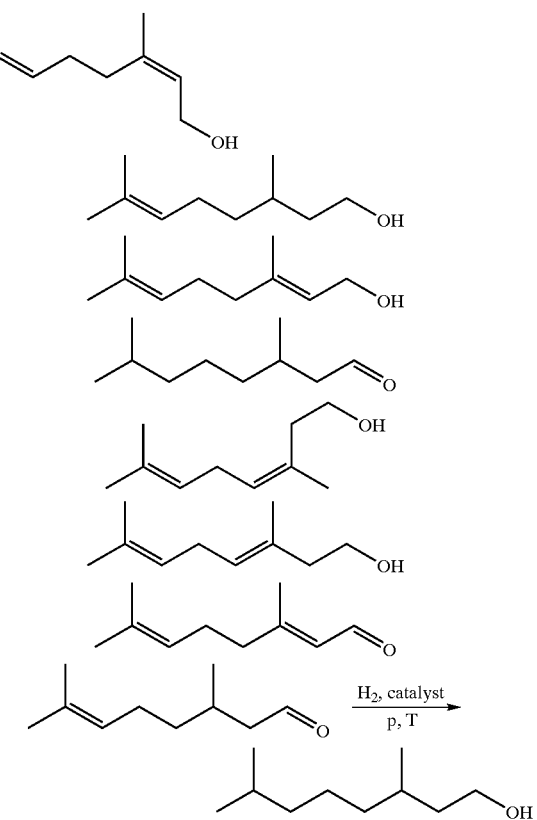

If, for example, the residues obtained from linalool synthesis (Table 1) are used, the total liquid phase concentration of linalool and geraniol/nerol of the residue or product mixture used is less than 30% by weight, preferably less than 20% by weight, particularly preferably less than 10% by weight. The total quantity of citronellol and isonerol is more than 50% by weight, preferably more than 80% by weight.

TABLE 1

| Typical residue from a linalool synthesis in % by weight: | |
|---|---|
| Low boilers | 0.10 |
| Tetrahydrolinalool | 0.00 |
| Linalool | 6.58 |
| Citronellol | 31.99 |
| Nerol | 0.57 |
| Citrate (cis/trans) | 1.04 |
| Tetrahydrogeraniol | 0.03 |
| Isonerol (I + II) | 54.60 |
| Others | 5.05 |

If, for example, the residues obtained from nerol/geraniol synthesis (Table 2) are used, the liquid phase content of usable products (geraniol and isonerols) is just under 60%.

TABLE 2

| Typical residue from a nerol/geraniol synthesis in % by weight %: | |
|---|---|
| Low boilers | 1 |
| Geraniol | 45 |
| Isonerol (I + II) | 13 |
| High boilers | 41 |

If, for example, the residues obtained from a citronellal synthesis (Table 3) are used, the liquid phase content of usable products is just below 90%.

TABLE 3

Typical residue from a citronellal synthesis in % by weight:

| | |
|---|---|
| Citral | 44 |
| Citronellal | 30 |
| Citronellol | 13 |
| High boilers | 11 |

If, for example, the residues obtained from a citronellol synthesis (Table 4) are used, the liquid phase content of usable products (geraniol and isonerol) is 95%.

TABLE 4

Typical residue from a citronellol synthesis in % by weight:

| | |
|---|---|
| Geraniol | 10 |
| Nerol | 5 |
| Citronellol | 75 |
| Dimethyloctanol | 5 |
| High boilers | 5 |

Suitable hydrogenation catalysts include in principle all hydrogenation catalysts that can be used for the hydrogenation of olefinic double bonds (eg. Houben Weyl, Methoden der organischen Chemie, Volume 4/1c).

Particularly suitable hydrogenation catalysts are catalysts that contain, as active components, elements selected from the group consisting of copper, silver, gold, iron, cobalt, nickel, rhenium, ruthenium, rhodium, palladium, osmium, iridium, platinum, chromium, molybdenum and tungsten, in each case in metallic form (eg. as Ra catalyst, oxidation state 0) or in the form of compounds, such as oxides, which are reduced to the corresponding metal under the process conditions.

The catalytically active components copper, silver, gold, iron, cobalt, nickel, rhenium, ruthenium, rhodium, palladium, osmium, iridium, platinum, chromium, molybdenum and/or tungsten are generally present in the catalytically active mass of the catalyst in quantities in the range from 0.1 to 80% by weight, preferably from 0.1 to 70% by weight, particularly preferably from 0.1 to 60% by weight, calculated as the metal in the oxidation state 0.

Preferred catalysts comprise elements as catalytically active components that are selected from the group consisting of copper, silver, cobalt, nickel, ruthenium, rhodium, palladium, platinum, chromium and molybdenum, in particular selected from the group consisting of copper, cobalt, nickel and palladium, in each case in metallic form (oxidation state 0) or in the form of compounds, such as oxides, which are reduced to the corresponding metal under the process conditions.

Particularly preferred catalysts are those with Co, Ni, Cu, Ru, Pd and/or Pt as active components. These can be used as unsupported catalysts, as supported catalysts or as activated metal catalysts (Raney catalysts).

The catalytically active mass of these preferred catalysts further comprises the support materials aluminum oxide ($Al_2O_3$), zirconium dioxide ($ZrO_2$), titanium dioxide ($TiO_2$), carbon and/or oxygen-containing compounds of silicon, in general in total quantities in the range from 20 to 99.9% by weight, preferably from 30 to 99.9% by weight, particularly preferably from 40 to 99.9% by weight, based on $SiO_2$.

Of the Raney catalysts, catalysts such as Ra—Ni are preferably used. Ra—Co, Ra—Co—Ni—Fe, Ra—Ni—Co—Fe—Cr or Ra—Ni and Ra—Co with doping of other transition metals are used in water-free form, or else in water-moist or solvent-free form.

The hydrogenation catalysts used in the process of the invention can be prepared by processes described in the prior art and can sometimes also be obtained commercially.

The hydrogenation can be carried out batchwise or continuously. To make comparatively large quantities (>500 t/a), a continuously operated hydrogenation is advisable.

The reaction can be carried out in a suspension or in a fixed bed. A continuously operated fixed bed variant can be operated by trickle or liquid-phase methods. Gas phase hydrogenation can also be considered.

Suspension hydrogenation can be carried out batchwise, generally in liquid phase.

For all variants, temperatures are chosen in the range from 20 to 250° C., preferably from 30 to 200° C., particularly preferably from 50 to 180° C.

The pressure is generally selected in the range from 1 to 250 bar, preferably from 5 to 200 bar, particularly preferably from 10 to 100 bar.

The hydrogenation by the process of the invention can be carried out either with or without a solvent, for example alcohols such as methanol, ethanol, propanol, butanol, aliphatic or aromatic hydrocarbons such as toluene, xylene, cyclohexane, ethers such as THF, dioxane, methyl tert-butyl ether.

However, it is preferred to carry out the hydrogenation without a solvent.

The examples which follow illustrate the invention.

Linalool Synthesis

At the bottom of the column, geraniol/nerol is isomerized to give linalool with a homogeneously dissolved catalyst and the linalool formed is continuously distilled off, so that a steady state linalool concentration of from 3 to 8% is set in the liquid phase. Geraniol/nerol is continuously added to the liquid phase at the same rate at which linalool is distilled off. High boilers, and also citronellol and isonerols build up in liquid phase. When a content of, for example, 20% by weight of high boilers, 16% by weight of citronellol and 24% by weight of isonerol I+II is attained, the addition of geraniol/nerol is ceased and the remaining geraniol/nerol in the liquid phase is further isomerized and distilled off as linalool. Isomerization is continued until the total liquid phase content of linalool, geraniol/nerol is 10% by weight or less.

The pressure is then continuously reduced from 135 mbar to 5 mbar (only by way of example) and citronellol and isonerols, together with the remaining linalool, are distilled off. Composition: 35% of lin, 31% of citronellol, 34% of isonerol I+II. The residue (see Examples 1 to 4) is then, according to the invention, hydrogenated there or somewhere else.

EXAMPLE 1

A 270 ml autoclave with a stirrer and catalyst basket was charged with 20 ml of catalyst 1 (preparation (0.47% of Pd on γ-aluminum oxide: the catalyst was prepared by saturation of γ-aluminum oxide extrudates (diameter of the extrudates: 4 mm) with an aqueous palladium nitrate solution. The Pd concentration in the saturating solution was set such that the extrudates were saturated to about 95% of their absorption capacity for water, and the precious metal content of 0.47% by weight based on the total weight of the finished catalyst results. The saturated extrudates were then dried at 120° C. for 12 h and calcined at 300° C. for 6 h). This was then heated to 280° C. under 10 l/h (STP) of hydrogen and then for 3 hours at 40 bar hydrogen pressure. 50 ml of the mixture 1 were then added to the reactor at RT. The reaction was carried out at 100° C. at a pressure of 40 bar.

Analysis: 30 m DBWAX 0.32 mm 0.25 μm 80° C.–3° C./min-230° C.-20 min

|  | Reactant mixture | Product mixture (3 h) | Product mixture (5 h) |
|---|---|---|---|
| Low boilers | 0.00 | 1.43 | 1.52 |
| Tetrahydrolinalool | 0.00 | 6.69 | 6.69 |
| Linalool | 6.58 | 0 | 0 |
| Citronellol | 31.99 | 0 | 0 |
| Nerol | 0.57 | 0.34 | 0.10 |
| Citrate (cis/trans) | 1.08 | 0.00 | 0 |
| Tetrahydrogeraniol | 0.03 | 85.27 | 85.63 |
| Isonerol (I + II) | 54.61 | 0.30 | 0.15 |
| Others | 4.60 | 5.94 | 5.95 |

The conversion (based on components which can be hydrogenated to give dimethyloctanol) was 99.6%. The selectivity was 98.3%.

EXAMPLE 2

A 270 ml autoclave with stirrer and catalyst basket was charged with 20 ml of catalyst 2 (NiO 21.5%, $Na_2O$ 0.35%, CuO 7.3%, $Mn_3O_4$ 2.0% and $H_3PO_4$ 1.2%, reduced-passivated at 190° C.). This was heated at atmospheric to 280° C. under 10 l/h (STP) of hydrogen and then for 3 h under 40 bar hydrogen pressure. 50 ml of the mixture 1 were then added to the reactor at RT. The reaction was carried out at 100° C. under a pressure of 40 bar.

Analysis: 30 m DBWAX 0.32 mm 0.25 μm 80° C.–3° C./min-230° C. -20 min

|  | Reactant mixture | Product mixture (3 h) | Product mixture (6 h) |
|---|---|---|---|
| Low boilers | 0.10 | 0.70 | 1.10 |
| Tetrahydrolinalool | 0.00 | 5.85 | 6.50 |
| Linalool | 6.58 | 0 | 0.00 |
| Citronellol | 31.99 | 4.60 | 0.30 |
| Nerol | 0.57 | 0.70 | 0.14 |
| Citrate (cis/trans) | 1.04 | 0 | 0.12 |
| Tetrahydrogeraniol | 0.03 | 79 | 86.3 |
| Isonerol (I + II) | 54.60 | 0 | 0.2 |
| Others | 5.05 | 8 | 5.40 |

The conversion (based on components which can be hydrogenated to give dimethyloctanol) was 98.9%. The selectivity was 98.7%.

EXAMPLE 3

A 270 ml autoclave with stirrer and catalyst basket was charged with 20 ml of catalyst 3 (catalyst A from EP 0963975 A1). This was heated at atmospheric to 280° C. under 10 l/h (STP) of hydrogen and then for 3 h under 40 bar hydrogen pressure. 50 ml of the mixture 1 were then added to the reactor at RT. The reaction was carried out at 180° C. under a pressure of 40 bar.

Analysis: 30 m DBWAX 0.32 mm 0.25 μm 80° C.–3° C./min-230° C. -20 min

|  | Reactant mixture | Product mixture (2 h) | Product mixture (4 h) |
|---|---|---|---|
| Low boilers | 0.10 | 4.28 | 7.32 |
| Tetrahydrolinalool | 0.00 | 6.41 | 6.44 |
| Linalool | 6.58 | 0.00 | 0.00 |
| Citronellol | 31.99 | 0.46 | 0.18 |
| Nerol | 0.57 | 0.3 | 0.10 |
| Citrate (cis/trans) | 1.04 | 0.22 | 0.09 |
| Tetrahydrogeraniol | 0.03 | 81.75 | 78.03 |
| Isonerol (I + II) | 54.60 | 0.28 | 0.15 |
| Others | 5.05 | 6.3 | 7.69 |

The conversion (based on components which can be hydrogenated to give dimethyloctanol) was 99.4%. The selectivity was 91.4%.

EXAMPLE 4

A 270 ml autoclave with stirrer and catalyst basket was charged with 20 ml of catalyst (catalyst A, Example 3). This was heated at atmospheric to 280° C. under 10 l/h (STP) of hydrogen and then for 3 h under 40 bar hydrogen pressure. 50 ml of the mixture 1 were then added to the reactor at RT. The reaction was carried out at 160° C. under a pressure of 40 bar.

Analysis: 30 m DBWAX 0.32 mm 0.25 μm 80° C.–3° C./min-230° C. -20 min

|  | Reactant mixture | Product mixture (2 h) | Product mixture (4 h) |
|---|---|---|---|
| Low boilers | 0.10 | 2.87 | 3.49 |
| Tetrahydrolinalool | 0.00 | 6.30 | 6.24 |
| Linalool | 6.58 | 0.00 | 0.00 |
| Citronellol | 31.99 | 0.08 | 0.08 |
| Nerol | 0.57 | 0.36 | 0.18 |
| Citrate (cis/trans) | 1.04 | 0.27 | 0.09 |
| Tetrahydrogeraniol | 0.03 | 82.17 | 80.55 |
| Isonerol (I + II) | 54.60 | 0.28 | 0.15 |
| Others | 5.05 |  |  |

The conversion (based on components which can be hydrogenated to give dimethyloctanol) was 99.4%. The selectivity was 95.9%.

EXAMPLE 5

0.1 g ml of catalyst were introduced to a 50 ml glass autoclave. The autoclave was purged three times with 5 bar argon and then 3* with 10 bar $H_2$: after which the reactants (10 g) were introduced. The reaction conditions are in the table.

Conditions:

| Run No. | Catalyst | Temperature ° C. | Pressure in bar | H2 consumption in bar | Reaction time in h |
|---|---|---|---|---|---|
| 1 | 5% Pd/C (Heraeus; 46% water; Type K-0293) | 85 | 20 | 8.1 | 2 |
| 2 | 5% Pd/C (see above) | 125 | 20 | 25 | 2 |

-continued

| Run No. | Catalyst | Temperature °C. | Pressure in bar | H2 consumption in bar | Reaction time in h |
|---|---|---|---|---|---|
| 3 | 10% Pd/C (Degussa; Type E10 N/D) | 125 | 20 | 20.5 | 2 |
| 4 | PtO$_2$ * H$_2$O (Fluka) | 125 | 20 | 3 | 2 |
| 5 | Pd/C H0-50 (DE 2936362) | 125 | 20 | 35 | 3 |
| 6 | Pd/C H0-50 | 130 | 20 | 81.5 | 5 |
| 7 | Pd/C H0-50 | 125 | 60 | not readable | 4 |

| Reactant | Run No. | | | | | | |
|---|---|---|---|---|---|---|---|
| | 1 | 2 | 3 | 4 | 5 | 6 | 7 |
| Low boilers | 0.82 | 3.10 | 19.41 | 18.92 | 1.0 | 11.55 | 8.76 | 9.94 |
| Linalool | 1.43 | 1.23 | 0.76 | 0.79 | 1.38 | 1.05 | — | — |
| Middle boilers | 1.51 | 10.10 | 18.58 | 16.80 | 2.62 | 18.51 | — | — |
| Citronellol | 57.35 | 54.63 | 37.76 | 35.84 | 57.05 | 36.88 | — | — |
| Nerol | 0.14 | 0.52 | — | — | 0.13 | — | — | — |
| Isonerol I | 28.56 | 17.43 | 0.08 | 0.16 | 25.50 | 0.12 | — | — |
| Isonerol II | 10.08 | 7.14 | 0.03 | 0.09 | 9.20 | 0.04 | — | — |
| Geraniol | 0.02 | 1.19 | 0.02 | 0.02 | 0.08 | 0.03 | — | — |
| High boilers | 0.06 | 0.02 | 2.50 | 3.48 | 0.56 | 1.05 | 1.00 | 0.49 |
| Tetrahydrogeraniol | — | 4.62 | 20.57 | 23.87 | 1.93 | 30.72 | 90.24 | 89.56 |

All analyses in GC area %.

GC/MS of sample 895 was carried out. Tetrahydrogeraniol (89.56%) and tetrahydrolinalool (7.80%), and also main low-boiling peak (2,6-dimethyloctane, 1.74%) were identified.

EXAMPLE 6

680 g of a reactant mixture consisting of 36% of citronellol, 58% of isonerol I+II, 4% of linalool and 4% of other compounds, and 6.8 g of Pd/C (5% Pd) were introduced to a 2.5 l autoclave and hydrogenated at 125° C. at 60 bar H$_2$ for about 5.5 h. The cooled reaction effluent was filtered to remove the catalyst and contained 92.2% of tetrahydrogeraniol and 4% of tetrahydrolinalool.

The filtered crude effluent was distilled at a liquid phase temperature of from 103–112° C. and 9–10 mbar at a reflux ratio of from 25:1 to 5:1. The fractionation gave 557 g of tetrahydrogeraniol having a content of >99% of good scent quality (b.p.: 98° C. at 9–10 mbar). Further tetrahydrogeraniol was present in the first cut and the distillation residue.

EXAMPLE 7

680 g of a reactant mixture consisting of 38% of citronellol, 56% of isonerol I+II, 5% of linalool and 3% of other compounds, and 5 g of Ra—Ni (Degussa) were introduced to a 2.5 l autoclave and hydrogenated at 100° C. at 90 bar H$_2$ for about 12 h. The cooled reaction effluent was filtered to remove the catalyst and contained 93.2% of tetrahydrogeraniol and 5% of tetrahydrolinalool.

We claim:

1. A process for the preparation of tetrahydrogeraniol, wherein the product mixtures and distillation residues resulting from linalool, citronellal, citronellol or geraniol/nerol synthesis are fed directly to catalytic hydrogenation.

2. The process as claimed in claim 1, wherein the product mixtures or distillation residues comprise more than one compound of the general formula (I)

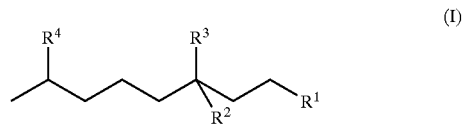

where

R$^1$ is OH, H, CH$_3$

R$^2$, R$^3$ are H, OH, CH$_3$

R$^4$ is H, CH$_3$, and one to four double bonds are present at any site in the molecule.

3. The process as claimed in claim 1, wherein the product mixtures or distillation residues comprise more than one compound selected from the group consisting of nerol, geraniol, isonerol 2, citral, citronellol, 3,7-dimethyloctanal, isonerol 1, citronellal and linalool.

4. The process as claimed in claim 1, wherein the distillation residue or product mixture from linalool synthesis is used.

5. The process as claimed in claim 4, wherein the total liquid phase content of linalool and geraniol/nerol is less than 30% by weight.

6. The process as claimed in claim 4, wherein the product mixture contains a total fraction of citronellol and isonerol of greater than 50% by weight.

7. The process as claimed in claim 1, wherein the hydrogenation is carried out using metal catalysts.

8. The process as claimed in claim 7, wherein the metal catalysts are selected from the metals of group VIIIA of the Periodic Table.

9. The process as claimed in claim 7, wherein the metal catalysts comprise Pd, Co or Ni.

10. The process as claimed in claim 7, wherein hydrogenation is carried out using Raney nickel.

* * * * *